(12) United States Patent
Pulapura et al.

(10) Patent No.: US 10,737,004 B2
(45) Date of Patent: Aug. 11, 2020

(54) DEVICES AND TREATMENTS FOR IMPLANTABLE DEVICES

(71) Applicant: TYRX, Inc., Monmouth Junction, NJ (US)

(72) Inventors: Satish Pulapura, Bridgewater, NJ (US); Fatima Buevich, Highland Park, NJ (US); Jorie Soskin, Edina, MN (US); Jonathan Sturtevant, Blaine, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 196 days.

(21) Appl. No.: 15/854,284

(22) Filed: Dec. 26, 2017

(65) Prior Publication Data

US 2018/0193540 A1 Jul. 12, 2018

Related U.S. Application Data

(60) Provisional application No. 62/445,512, filed on Jan. 12, 2017.

(51) Int. Cl.
*A61M 1/10* (2006.01)
*A61L 27/54* (2006.01)
(Continued)

(52) U.S. Cl.
CPC .......... *A61M 1/1006* (2014.02); *A61L 27/04* (2013.01); *A61L 27/14* (2013.01); *A61L 27/34* (2013.01);
(Continued)

(58) Field of Classification Search
CPC .. A61M 1/1006; A61M 1/1008; A61M 1/122; A61M 1/127; A61M 25/05; A61M 2205/0266; A61M 2205/8206; A61L 27/14; A61L 27/134; A61L 27/154; A61L 29/02; A61L 29/085; A61L 29/146; A61L 29/16; A61L 2300/406; A61L 2400/16; A61L 2430/20
See application file for complete search history.

(56) References Cited

U.S. PATENT DOCUMENTS

2001/0016726 A1* 8/2001 Dubrul .................... A61F 2/958
604/509
2008/0128315 A1 6/2008 Buevich
(Continued)

FOREIGN PATENT DOCUMENTS

WO 2015038875 A1 3/2015
WO 2017192491 A1 11/2017

OTHER PUBLICATIONS

International Search Report and Written Opinion of the International Searching Authority, European Patent Office, PCT/US2017/068407, dated Jul. 25, 2019.
(Continued)

*Primary Examiner* — Paula J Stice
(74) *Attorney, Agent, or Firm* — Sorell, Lenna & Schmidt, LLP

(57) ABSTRACT

A medical prosthesis includes a tube having a length between a first end and a second end. The tube includes a polymer and at least one drug. The tube is configured to be manipulated to selectively increase and decrease the length of the tube. Kits, systems and methods are disclosed.

20 Claims, 12 Drawing Sheets

(51) Int. Cl.
*A61L 27/04* (2006.01)
*A61L 27/34* (2006.01)
*A61L 27/14* (2006.01)
*A61M 1/12* (2006.01)
*A61L 29/08* (2006.01)
*A61L 29/02* (2006.01)
*A61L 29/16* (2006.01)
*A61L 29/14* (2006.01)
*A61M 25/00* (2006.01)

(52) U.S. Cl.
CPC ............... *A61L 27/54* (2013.01); *A61L 29/02* (2013.01); *A61L 29/085* (2013.01); *A61L 29/146* (2013.01); *A61L 29/16* (2013.01); *A61M 1/1008* (2014.02); *A61M 1/122* (2014.02); *A61M 1/127* (2013.01); *A61L 2300/406* (2013.01); *A61L 2400/16* (2013.01); *A61L 2430/20* (2013.01); *A61M 25/005* (2013.01); *A61M 2205/0266* (2013.01); *A61M 2205/8206* (2013.01)

(56) References Cited

U.S. PATENT DOCUMENTS

| | | | |
|---|---|---|---|
| 2010/0168808 A1* | 7/2010 | Citron | A61L 31/10 607/5 |
| 2015/0086604 A1* | 3/2015 | Buevich | C08L 67/04 424/426 |
| 2016/0250447 A1* | 9/2016 | Sos | A61M 25/0905 604/510 |
| 2018/0200185 A1* | 7/2018 | Labib | A61L 31/16 |

OTHER PUBLICATIONS

International Search Report and Written Opinion of the International Searching Authority (EPO) dated Apr. 18, 2018 of International Application No. PCT/US2017/068407 filed on Dec. 26, 2017.

* cited by examiner

Graph 1

Graph 2

DEVICES AND TREATMENTS FOR IMPLANTABLE DEVICES

TECHNICAL FIELD

The present disclosure generally relates to devices, systems and methods including a medical prosthesis that covers at least a portion of an implantable device, wherein the medical prosthesis comprises at least one drug to prevent, mitigate and/or treat infection.

BACKGROUND

There is a staggering gap in the number of patients with congestive heart failure and the number of available heart transplants. According to recent reports, there are about 5 million patients with congestive heart failure, resulting in over 250,000 deaths every year. The number of available heart transplants is only about 2,000. The use of left ventricular assist devices (LVADs) has helped bridge this gap. An LVAD is an implantable device that is used to assist the functioning of a failing heart. LVADs include a pump that connects the left ventricle to the aorta which pulls blood from the left ventricle and pumps it into the aorta. The pump is connected by a percutaneous drive line with an electrical wire to an external battery pack, which provides power to the pump. LVADs have evolved from the first generation which used volume-displacement pumps through axial flow pumps, to the latest continuous flow centrifugal pumps. Infection rates associated with LVADs are extremely high. A recent review from the Mayo Clinic reported that the infection rate for first-generation LVADs vary from 25 to 80%, and for second generation 30 to 50%. It has been determined that sepsis (infection) caused twice as many deaths as device failure. Infections also increase the cost to the healthcare system.

Therefore, there is a need for treatment modalities for preventing infection in connection with LVADs. Traditional means of preventing infection include treating the incision site at the time an LVAD is implanted. However, such treatments are not sufficient to prevent infection since the drive line offers a conduit from the outside to the LVAD and surrounding tissue. This disclosure describes an improvement over these prior art technologies.

SUMMARY

In one embodiment, in accordance with the principles of the present disclosure, a medical prosthesis is provided that includes a tube having a length between a first end and a second end. The tube includes a polymer and at least one drug. The tube is configured to be manipulated to selectively increase and decrease the length of the tube. Kits, systems and methods are disclosed. In some embodiments, the polymer includes the drug(s). In some embodiments, the drug(s) is/are coated or otherwise applied to the tube.

In one embodiment, in accordance with the principles of the present disclosure, a system is provided that includes the medical prosthesis discussed in the preceding paragraph and an implantable medical device. The medical prosthesis comprises a pouch coupled to the first end of the tube. The pouch comprises an inner cavity that is in communication with a passageway defined by the tube. The pouch comprises the polymer and the at least one drug. The implantable medical device is a left ventricular assist device comprising a pump and a drive line that is connected to the pump. The pouch covers at least a portion of the pump and the tube covers at least a portion of the drive line.

In one embodiment, in accordance with the principles of the present disclosure, a system is provided that includes a left ventricular assist device comprising a pump and a drive line that is connected to the pump. The drive line comprises an electrical wire that is connected to the pump. The electrical wire is connected to a battery. The system includes a medical prosthesis having a tube and a pouch that is coupled to the tube. The tube has a length between a first end and a second end. The tube and the pouch comprise a tyrosine-derived polyarylate polymer. The polymer comprises rifampin and minocycline. The polymer comprises a plurality of strips that are woven in a biaxial braid to form the tube. At least a portion of the pump is positioned within the pouch and the drive line is positioned within the tube. The tube extends from the pump to the battery.

In one embodiment, in accordance with the principles of the present disclosure, a method of preventing, mitigating, or treating infection is provided. The method comprises positioning a pump of an implantable medical device within a pouch of a medical prosthesis, the medical prosthesis comprising a polymer, the polymer comprising at least one drug. A drive line of the implantable medical device is positioned within a tube of the medical prosthesis, the drive line comprising an electrical wire that is connected to the pump, the tube being connected to the pouch. The implantable medical device is implanted within a patient such that a portion of the drive line and a battery of the implantable medical device are positioned outside of the patient.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

The present disclosure will become more readily apparent from the specific description accompanied by the following drawings, in which.

DETAILED DESCRIPTION

Figure 1:
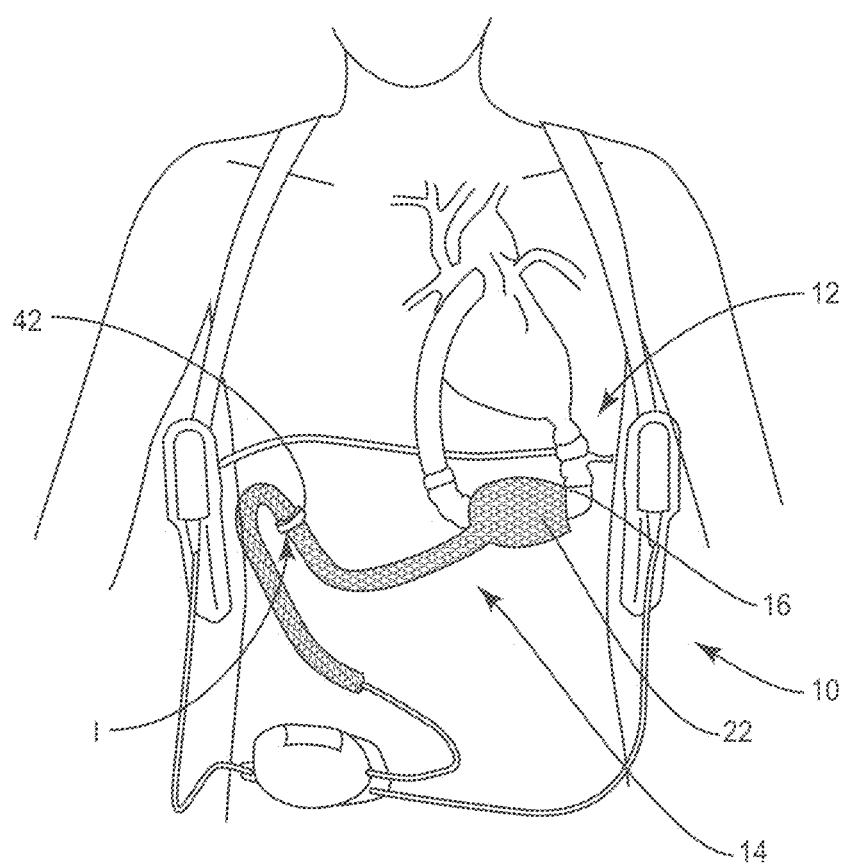
FIG. 1 is a plan view of components of one embodiment of a system in accordance with the principles of the present disclosure.

For the purposes of this specification and appended claims, unless otherwise indicated, all numbers expressing quantities of ingredients, percentages or proportions of materials, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

This disclosure is directed to surgical systems, such as, for example, surgical system 10. In some embodiments, the components of system 10 can be fabricated from biologically acceptable materials suitable for medical applications, including metals, synthetic polymers, and/or ceramics, depending on the particular application and/or preference of a medical practitioner. For example, the components of system 10, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

System 10 includes an implantable device 12 and a medical prosthesis 14, as shown in FIG. 1. Prosthesis 14 is configured to cover at least a portion of device 12 to prevent, mitigate and/or treat infection, as discussed herein. In one embodiment, device 12 is a heart assist device, such as, for example, a left ventricular assist device (LVAD). It is contemplated that device 12 may include any implantable device, such as, for example, artificial hearts, cardiac jackets, implantable defibrillators, electrostimulation devices and leads (including pacemakers, lead adapters and lead connectors), implanted medical device power supplies, peripheral cardiovascular devices, atrial septal defect closures, left atrial appendage filters, valve annuloplasty devices, mitral valve repair devices, vascular intervention devices, ventricular assist pumps, and vascular access devices (including parenteral feeding catheters, vascular access ports, central venous access catheters); surgical devices such as cerebro-spinal fluid shunts, shunts for hydrocephalus, drainage tubes, catheters including thoracic cavity suction drainage catheters, abscess drainage catheters, biliary drainage products, and implantable pumps; drug delivery devices such as drug delivery pumps, implanted drug infusion tubes, drug infusion catheters, and intravitreal drug delivery devices; glaucoma drain shunts and intraocular lenses; urological devices such as penile devices (e.g., impotence implants), sphincter, urethral, prostate, and bladder devices (e.g., incontinence devices, benign prostate hyperplasia management devices, prostate cancer implants, etc.), urinary catheters including indwelling ("Foley") and non-indwelling urinary catheters, and renal devices; synthetic prostheses such as artificial organs (e.g., pancreas, liver, lungs, heart, etc.); respiratory devices including lung catheters; neurological devices such as neurostimulators, neurological catheters, neurovascular balloon catheters, neuro-aneurysm treatment coils, and neuro-patches; splints, laryngectomy tubes, esophageal tubes, salivary bypass tubes, and tracheostomy tubes; oncological implants; and pain management implants.

Figure 2:
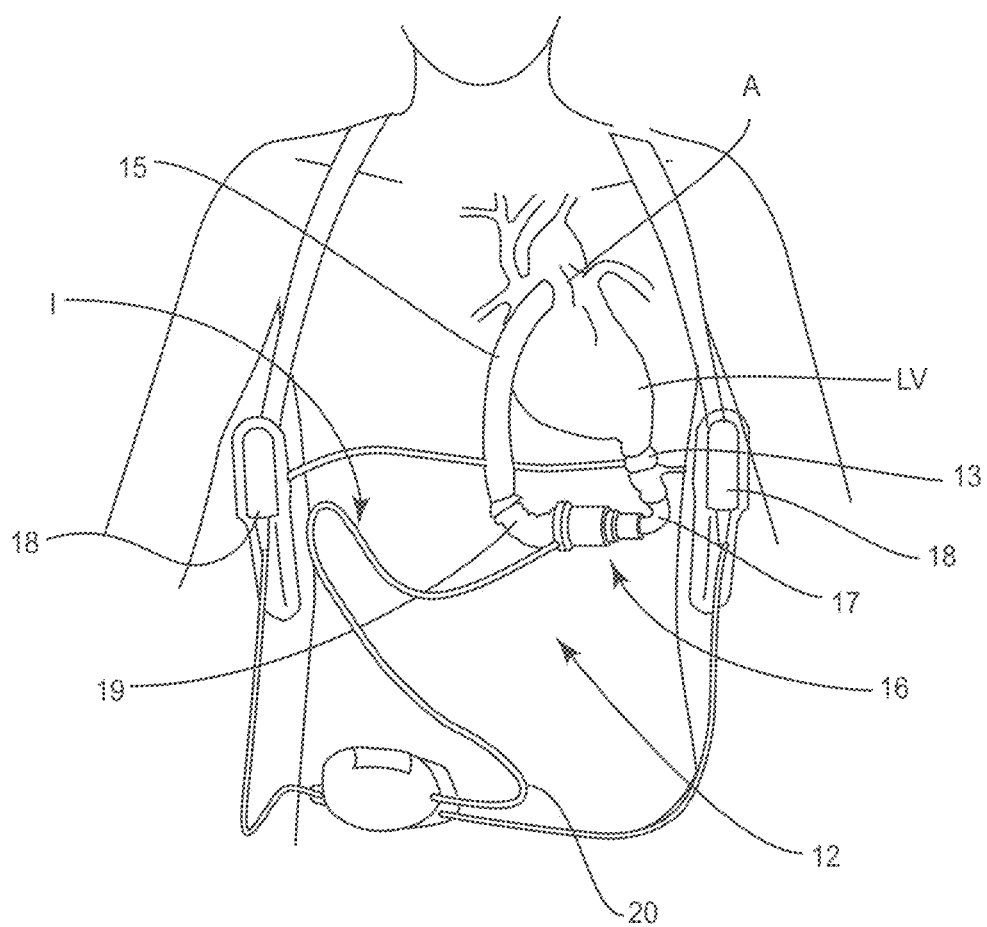
FIG. 2 is a plan view of components of the system shown in FIG. 1.

As shown in FIG. 2, device 12 includes a heart pump 16 that connects the left ventricle LV to aorta A. Pump 16 pulls blood from left ventricle LV and pumps it into aorta A. Device 12 includes a conduit 13 that is configured to be attached to left ventricle LV and a conduit 15 that is connected to aorta A. An inflow valve 17 connects pump 16 with conduit 13. An outflow valve 19 connects pump 16 with conduit 15. Pump 16 is connected to at least one battery pack 18 by a percutaneous lead or drive line 20. Drive line 20 includes an electrical wire that provides power to pump 16. Drive line 20 exits a patient's body through an incision, such as, for example, incision I shown in FIG. 2 such that battery pack 18 is positioned outside of the patient's body.

Figure 3:
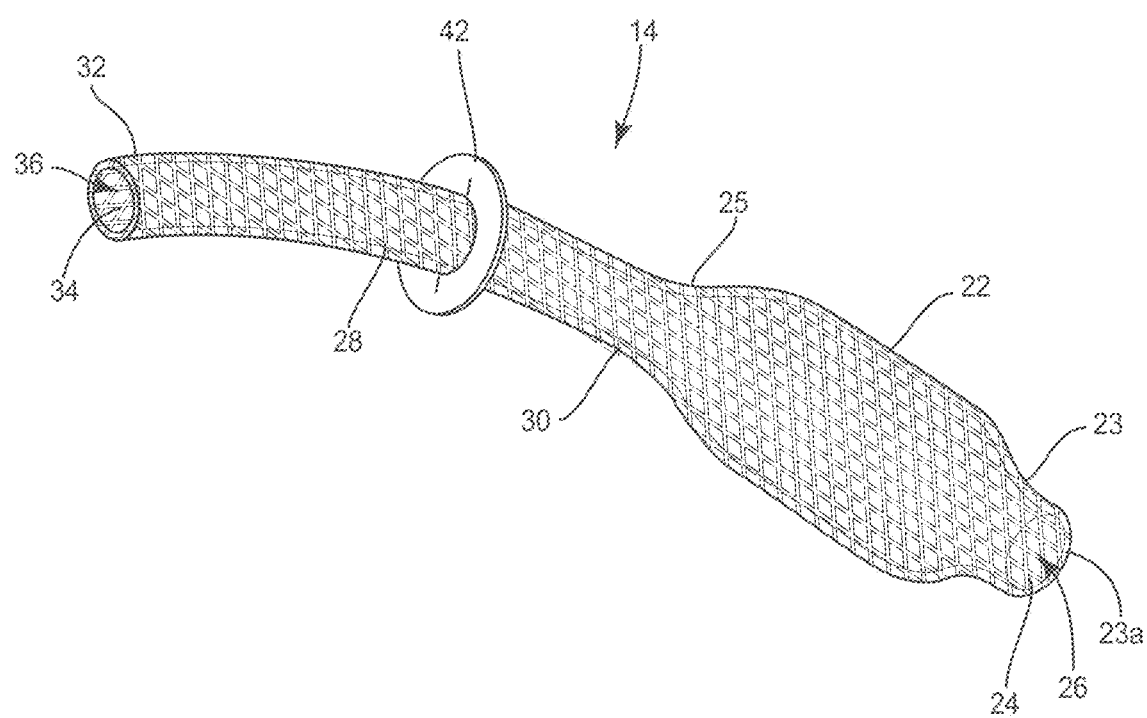
FIG. 3 is a perspective view of components of the system shown in FIG. 1.
Figure 6:
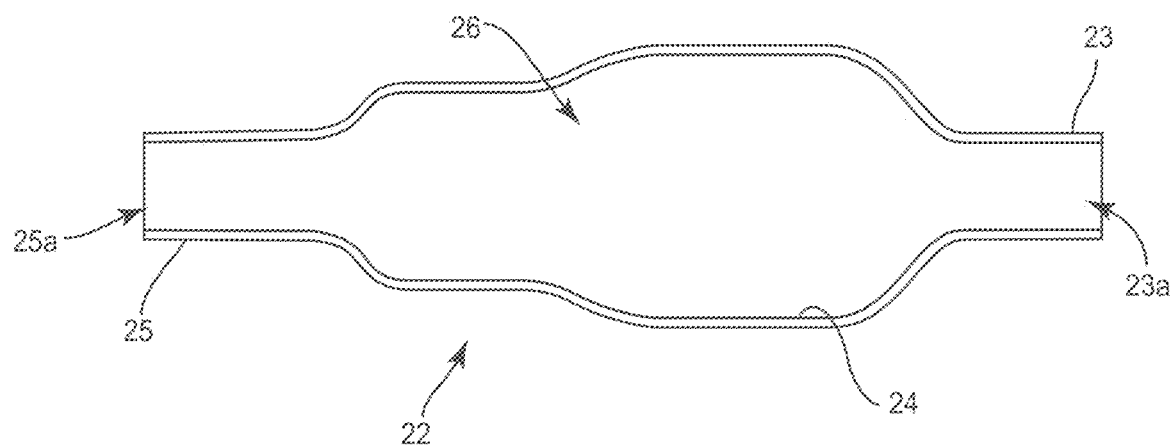
FIG. 6 is a side, cross sectional view of the component shown in FIG. 5.

Prosthesis 14 includes a main body, such as, for example, a pouch 22, as shown in FIG. 3. Pouch 22 includes an end 23 and an opposite end 25. Pouch 22 has a length defined by the distance from end 23 to end 25. Pouch 22 includes an inner surface 24 that defines an inner cavity 26. Cavity 26 is configured for disposal of at least a portion of pump 16. In some embodiments, cavity 26 is configured for disposal of pump 16 and at least a portion of valve 17 and/or valve 19. In some embodiments, cavity 26 is configured for disposal of pump 16 and at least a portion of conduit 13 and/or conduit 15. Pouch 22 includes an opening 23a in end 23 and an opening 25a in end 25 (FIG. 6). Openings 23a, 25a are in communication with cavity 26.

Prosthesis 14 includes a tube 28 that extends from pouch 22. Tube 28 includes an end 30 that is coupled directly to pouch 22 and an opposite end 32. End 30 of tube 28 is coupled to end 25 of pouch 22, as shown in FIG. 3. Tube 28 has a length defined by the distance from end 30 to end 32. Tube 28 is configured to be manipulated to selectively increase and decrease the length of tube 28, as discussed herein. End 30 defines a first section of tube 28 and end 32 defines a second section of tube 28 that is coupled to the first section. An inner surface 34 of tube 28 defines a passageway 36 configured for disposal of at least a portion of drive line 20. Tube 28 includes an opening in end 30 and an opening in end 32. The opening in end 30 of tube 28 is in communication with opening 25a in end 25 of pouch 22 such that passageway 36 is in communication with cavity 26. In some embodiments, passageway 36 is configured for disposal of at least a portion of drive line 20 and a portion of pump 16. Tube 28 is flexible such that tube 28 may be selectively bent along the length of tube 28. For example, tube 28 may be moved from a linear configuration in which tube 28 extends parallel or substantially parallel to a longitudinal axis along the entire length of tube 28, as shown in FIG. 3, to a second configuration in which one or more sections extend transverse to the longitudinal axis, as shown in FIG. 1.

In some embodiments, tube 28 and pouch 22 are integrally formed. For example, tube 28 and pouch 22 may be formed from strips of material, such as, for example, one or more polymers, that extend continuously from pouch 22 to tube 28. That is, one or more of the strips may form a portion of pouch 22 and a portion of tube 28. In some embodiments, tube 28 and pouch 22 are formed separately and are then connected to one another. For example, tube 28 may be attached to pouch 22 by bonding or an adhesive. In some embodiments, tube 28 is permanently attached to pouch 22 such that tube 28 cannot be removed from pouch 22 without cutting tube 28 from pouch 22, for example. In some embodiments, tube 28 is removeably coupled to pouch 22 such that tube 28 can be removed from pouch 22 without cutting tube 28 from pouch 22. In some embodiments, tube 28 is not attached to pouch 22 such that tube 28 is spaced apart from pouch 22.

In some embodiments, at least a portion of prosthesis 14, such as, for example, pouch 22 or tube 28 is made from a polymer. In some embodiments, pouch 22 and tube 28 are both made from a polymer. In some embodiments, the polymer is selected from the group consisting of polylactic acid, polyglycolic acid, poly(L-lactide), poly(D,L-lactide), polyglycolic acid[polyglycolide], poly(L-lactide-co-D,L-lactide), poly(L-lactide-co-glycolide), poly(D, L-lactide-co-glycolide), poly(glycolide-co-trimethylene carbonate), poly (D,L-lactide-co-caprolactone), poly(glycolide-co-caprolactone), polyethylene oxide, polydioxanone, polypropylene fumarate, poly(ethyl glutamate-co-glutamic acid), poly(tert-butyloxy-carbonylmethyl glutamate), polycaprolactone, polycaprolactone co-butylacrylate, polyhydroxybutyrate, copolymers of polyhydroxybutyrate, poly (phosphazene), poly(phosphate ester), poly(amino acid), polydepsipeptides, maleic anhydride copolymers, polyiminocarbonates, poly[(97.5% dimethyl-trimethylene carbonate)-co-(2.5% trimethylene carbonate)], poly(orthoesters), tyrosine-derived polyarylates, tyrosine-derived polycarbonates, tyrosine-derived polyiminocarbonates, tyrosine-derived polyphosphonates, polyethylene oxide, polyethylene glycol, polyalkylene oxides, hydroxypropylmethylcellulose, polysaccharides such as hyaluronic acid, chitosan and regenerate cellulose. In some embodiments, the polymer may include combinations, blends or mixtures of the polymers discussed herein.

In some embodiments, the polymer is a polyarylate. In some embodiments, the polymer is a tyrosine-derived polyarylate. In some embodiments, the tyrosine-derived polyarylate is p(DTE co X % DT succinate), where X is about 10% to about 30%. In some embodiments, the tyrosine-derived polyarylate is p(DTE co X % DT succinate), where X ranges from about 26.5% to about 28.5%. In some embodiments, the tyrosine-derived polyarylate is p(DTE co X % DT succinate), where X is about 27.5%. In some embodiments, the polymer is P22-27.5 DT. In some embodiments, the polymer is p22-27.5 DT.

As used herein, DTE is the diphenol monomer desaminotyrosyl-tyrosine ethyl ester; DTBn is the diphenol monomer desaminotyrosyl-tyrosine benzyl ester; DT is the corresponding free acid form, namely desaminotyrosyl-tyrosine. BTE is the diphenol monomer 4-hydroxy benzoic acid-tyrosyl ethyl ester; BT is the corresponding free acid form, namely 4-hydroxy benzoic acid-tyrosine.

P22 is a polyarylate copolymer produced by condensation of DTE with succinate. P22-10, P22-15, P22-20, P22-xx, etc., represents copolymers produced by condensation of (1) a mixture of DTE and DT using the indicated percentage of DT (i.e., 10, 15, 20 and xx % DT, etc.) with (2) succinate.

In some embodiments, the polymer includes one or more polyarylates that are copolymers of desaminotyrosyl-tyrosine (DT) and a desaminotyrosyl-tyrosyl ester (DT ester), wherein the copolymer comprises from about 0.001% DT to about 80% DT and the ester moiety can be a branched or unbranched alkyl, alkylaryl, or alkylene ether group having up to 18 carbon atoms, any group of which can, optionally have a polyalkylene oxide therein. Similarly, another group of polyarylates are the same as the foregoing but the desaminotyrosyl moiety is replaced by a 4-hydroxybenzoyl moiety. In some embodiments, the DT or BT contents include those copolymers with from about 1% to about 30%, from about 5% to about 30%, or from about 10 to about 30%

DT or BT. In some embodiments, the diacids (used in forming the polyarylates) include succinate, glutarate and glycolic acid.

In some embodiments, the polymer includes one or more biodegradable, resorbable polyarylates and polycarbonates. These polymers, include, but are not limited to, BTE glutarate, DTM glutarate, DT propylamide glutarate, DT glycineamide glutarate, BTE succinate, BTM succinate, BTE succinate PEG, BTM succinate PEG, DTM succinate PEG, DTM succinate, DT N-hydroxysuccinimide succinate, DT glucosamine succinate, DT glucosamine glutarate, DT PEG ester succinate, DT PEG amide succinate, DT PEG ester glutarate, DT PEG ester succinate, DTMB P(Desaminotyrsoyl tyrosine methylparaben ester-glutarate), and DTPP P(Desaminotyrsoyl tyrosine propylparaben ester-glutarate).

In some embodiments, the polymer is one or more polymers from the DTE-DT succinate family of polymers, e.g., the P22-xx family of polymers having from 0-50%, 5-50%, 5-40%, 1-30% or 10-30% DT, including but not limited to, about 1, 2, 5, 10, 15, 20, 25, 27.5, 30, 35, 40, 45 and 50% DT. In some embodiments, the polymer is P22-27.5 DT.

In some embodiments, the polymer has diphenol monomer units that are copolymerized with an appropriate chemical moiety to form a polyarylate, a polycarbonate, a poly-iminocarbonate, a polyphosphonate or any other polymer.

In some embodiments, the polymer is tyrosine-based polyarylate. In some embodiments, the polymer includes blends and copolymers with polyalkylene oxides, including polyethylene glycol (PEG).

In some embodiments, the polymer can have from 0.1-99.9% PEG diacid to promote the degradation process. In some embodiments, the polymer includes blends of polyarylates or other biodegradable polymers with polyarylates.

In some embodiments, the polymer includes at least one drug, such as, for example, at least one active pharmaceutical ingredient. The polymer is configured to release the active pharmaceutical ingredient as the polymer degrades. In some embodiments, the polymer and/or the active pharmaceutical ingredient may be configured to reduce and/or inhibit bacterial attachment and/or biofilm formation.

The active pharmaceutical ingredient can include one or a combination of active pharmaceutical ingredients, such as, for example, anesthetics, antibiotics, anti-inflammatory agents, procoagulant agents, fibrosis-inhibiting agents, antiseptics, anti-scarring agents, leukotriene inhibitors/antagonists, cell growth inhibitors and mixtures thereof. In some embodiments, the active pharmaceutical ingredient includes one or more of the agents discussed in Fibrinolytics and Antifibrinolytics, Volume 46; 1978. Fritz Markwardt. Springer-Verlag, Jan. 1, 1978, which is incorporated herein by reference, in its entirety. In some embodiments, the active pharmaceutical ingredient is an antibiotic. In some embodiments, the antibiotic is selected from the group consisting of rifampin and minocycline and mixtures thereof.

Examples of non-steroidal anti-inflammatories include, but are not limited to, naproxen, ketoprofen, ibuprofen as well as diclofenac; celecoxib; sulindac; diflunisal; piroxicam; indomethacin; etodolac; meloxicam; r-flurbiprofen; mefenamic; nabumetone; tolmetin, and sodium salts of each of the foregoing; ketorolac bromethamine; ketorolac bromethamine tromethamine; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, l, and racemic isomers); and the methyl, ethyl, propyl, isopropyl, n-butyl, sec-butyl, t-butyl, esters of acetylsalicylic acid.

Examples of anesthetics include, but are not limited to, lidocaine, bupivacaine, and mepivacaine. Further examples of analgesics, anesthetics and narcotics include, but are not limited to acetaminophen, clonidine, benzodiazepine, the benzodiazepine antagonist flumazenil, lidocaine, tramadol, carbamazepine, meperidine, zaleplon, trimipramine maleate, buprenorphine, nalbuphine, pentazocain, fentanyl, propoxyphene, hydromorphone, methadone, morphine, levorphanol, and hydrocodone. Local anesthetics have weak antibacterial properties and can play a dual role in the prevention of acute pain and infection.

Examples of antibacterial agents or antimicrobials include, but are not limited to, triclosan, chlorohexidine and other cationic biguanides, rifampin, minocycline (or other tetracycline derivatives), vancomycin, gentamycin, gendine, genlenol, genfoctol, clofoctol, cephalosporins and the like. Further antibacterial agents or antimicrobials include aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; hexachlorophene; cefamandole nafate; cefepime and its hydrochloride, sulfate, and phosphate salt; cefdinir and its sodium salt; ceftriaxone and its sodium salt; cefixime and its sodium salt; cetylpyridinium chloride; ofoxacin; linexolid; temafloxacin; fleroxacin; enoxacin; gemifloxacin; lomefloxacin; astreonam; tosufloxacin; clinafloxacin; cefpodoxime proxetil; chloroxylenol; methylene chloride, iodine and iodophores (povidone-iodine); nitrofurazone; meropenem and its sodium salt; imipenem and its sodium salt; cilastatin and its sodium salt; azithromycin; clarithromycin; dirithromycin; erythromycin and hydrochloride, sulfate, or phosphate salts ethylsuccinate, and stearate forms thereof, clindamycin; clindamycin hydrochloride, sulfate, or phosphate salt; lincomycin and hydrochloride, sulfate, or phosphate salt thereof, tobramycin and its hydrochloride, sulfate, or phosphate salt; streptomycin and its hydrochloride, sulfate, or phosphate salt; vancomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; α-terpineol; thymol; taurinamides; nitrofurantoin; silver-sulfadiazine; hexetidine; methenamine; aldehydes; azylic acid; silver; benzyl peroxide; alcohols; carboxylic acids; salts; nafcillin; ticarcillin and its disodium salt; sulbactam and its sodium salt; methylisothiazolone, moxifloxacin; amifloxacin; pefloxacin; nystatin; carbepenems; lipoic acids and its derivatives; beta-lactams antibiotics; monobactams; aminoglycosides; microlides; lincosamides; glycopeptides; tetracyclines; chloramphenicol; quinolones; fucidines; sulfonamides; macrolides; ciprofloxacin; ofloxacin; levofloxacins; teicoplanin; mupirocin; norfloxacin; sparfloxacin; ketolides; polyenes; azoles; penicillins; echinocandines; nalidixic acid; rifamycins; oxalines; streptogramins; lipopeptides; gatifloxacin; trovafloxacin mesylate; alatrofloxacin mesylate; trimethoprims; sulfamethoxazole; demeclocycline and its hydrochloride, sulfate, or phosphate salt; doxycycline and its hydrochloride, sulfate, or phosphate salt; minocycline and its hydrochloride, sulfate, or phosphate salt; tetracycline and its hydrochloride, sulfate, or phosphate salt; oxytetracycline and its hydrochloride, sulfate, or phosphate salt; chlortetracycline and its hydrochloride, sulfate, or phosphate salt; metronidazole; dapsone; atovaquone; rifabutin; linezolide; polymyxin B and its hydrochloride, sulfate, or phosphate salt; sulfacetamide and its sodium salt; and clarithromycin (and combinations thereof). In some embodiments the polymer may contain rifampin and another antimicrobial agent, such as, for example, an antimicrobial agent that is a tetracycline derivative. In some embodiments, the polymer contains a cephalosporin and another antimicrobial agent. In some embodiments, the polymer contains combinations including rifampin and gentamycin, and rifampin and minocycline.

When a mixture of two antibiotics is used, they generally present in a ratio ranging from about 10:1 to about 1:10. In some embodiments, a mixture of rifampin and minocycline are used. In those embodiments, a ratio of rifampin to minocycline ranges from about 5:2 to about 2:5. In other embodiments, the ratio of rifampin to minocycline is about 1:1.

Examples of antifungals include amphotericin B; pyrimethamine; flucytosine; caspofungin acetate; fluconazole; griseofulvin; terbinafine and its hydrochloride, sulfate, or phosphate salt; amorolfine; triazoles (Voriconazole); flutrimazole; cilofungin; LY303366 (echinocandines); pneumocandin; imidazoles; omoconazole; terconazole; fluconazole; amphotericin B, nystatin, natamycin, liposomal amptericin B, liposomal nystatins; griseofulvin; BF-796; MTCH 24; BTG-137586; RMP-7/Amphotericin B; pradimicins; benanomicin; ambisome; ABLC; ABCD; Nikkomycin Z; flucytosine; SCH 56592; ER30346; UK 9746; UK 9751; T 8581; LY121019; ketoconazole; micronazole; clotrimazole; econazole; ciclopirox; naftifine; and itraconazole.

In some embodiments, the active pharmaceutical ingredient includes keflex, acyclovir, cephradine, malphalen, procaine, ephedrine, adriamycin, daunomycin, plumbagin, atropine, quinine, digoxin, quinidine, biologically active peptides, cephradine, cephalothin, cis-hydroxy-L-proline, melphalan, penicillin V, aspirin, nicotinic acid, chemodeoxycholic acid, chlorambucil, paclitaxel, sirolimus, cyclosporins, 5-fluorouracil and the like.

In some embodiments, the active pharmaceutical ingredient includes one or more ingredients that act as angiogenesis inhibitors or inhibit cell growth such as epidermal growth factor, PDGF, VEGF, FGF (fibroblast growth factor) and the like. These ingredients include anti-growth factor antibodies (neutrophilin-1), growth factor receptor-specific inhibitors such as endostatin and thalidomide. Examples of useful proteins include cell growth inhibitors such as epidermal growth factor.

Examples of anti-inflammatory compounds include, but are not limited to, anecortive acetate; tetrahydrocortisol, 4,9(11)-pregnadien-17α,21-diol-3,20-dione and its -21-acetate salt; 111-epicortisol; 17α-hydroxyprogesterone; tetrahydrocortexolone; cortisone acetate; hydrocortisone; hydrocortisone acetate; fludrocortisone; fludrocortisone acetate; fludrocortisone phosphate; prednisone; prednisolone; prednisolone sodium phosphate; methylprednisolone; methylprednisolone acetate; methylprednisolone, sodium succinate; triamcinolone; triamcinolone-16,21-diacetate; triamcinolone acetonide and its -21-acetate, -21-disodium phosphate, and -21-hemisuccinate forms; triamcinolone benetonide; triamcinolone hexacetonide; fluocinolone and fluocinolone acetate; dexamethasone and its -21-acetate, -21-(3,3-dimethylbutyrate), -21-phosphate disodium salt, -21-diethylaminoacetate, -21-isonicotinate, -21-dipropionate, and -21-palmitate forms; betamethasone and its -21- acetate, -21-adamantoate, -17-benzoate, -17,21-dipropionate, -17-valerate, and -21-phosphate disodium salts; beclomethasone; beclomethasone dipropionate; diflorasone; diflorasone diacetate; mometasone furoate; and acetazolamide.

Examples of leukotriene inhibitors/antagonists include, but are not limited to, leukotriene receptor antagonists such as acitazanolast, iralukast, montelukast, pranlukast, verlukast, zafirlukast, and zileuton.

In some embodiments, the active pharmaceutical ingredient includes sodium 2-mercaptoethane sulfonate ("MESNA"). MESNA has been shown to diminish myofibroblast formation in animal studies of capsular contracture with breast implants [Ajmal et al. (2003) Plast. Reconstr. Surg. 112:1455-1461] and may thus act as an anti-fibrosis agent.

Procoagulants include, but are not limited to, zeolites, thrombin, and coagulation factor concentrates.

In some embodiments, the amount of the active pharmaceutical ingredient included in the polymer ranges between about 0.3 to about 2.8 micrograms/cm$^2$. In other embodiments, the amount of the active pharmaceutical ingredient included in the polymer ranges between about 0.6 to about 1.4 micrograms/cm$^2$. In other embodiments, the amount of active pharmaceutical ingredient included in the polymer ranges between about 0.85 to about 1.20 micrograms/cm$^2$. In yet further embodiments, the amount of the active pharmaceutical ingredient included in the polymer ranges between about 0.90 to about 1.10 micrograms/cm$^2$.

In other embodiments, the active pharmaceutical ingredient includes rifampin and minocycline and the amount of each of rifampin and minocycline included in the polymer ranges between about 0.6 to about 1.4 micrograms/cm$^2$. In other embodiments, the amount of each of rifampin and minocycline that is included in the polymer ranges between about 0.85 to about 1.20 micrograms/cm$^2$. In further embodiments, the amount of each of rifampin and minocycline that is included in the polymer ranges between about 0.90 to about 1.10 micrograms/cm$^2$.

The active pharmaceutical ingredient may include any of the active pharmaceutical ingredients discussed herein. Doses of the active pharmaceutical ingredients discussed herein are known and the amounts of any single active pharmaceutical ingredient included in the polymer can readily be surmised. Any pharmaceutically acceptable form of the active pharmaceutical ingredients discussed herein can be employed in the polymer, e.g., the free base or a pharmaceutically acceptable salt or ester thereof. Pharmaceutically acceptable salts, for instance, include sulfate, lactate, acetate, stearate, hydrochloride, tartrate, maleate, citrate, phosphate and the like.

The polymer is configured to release the active pharmaceutical ingredient over time, as discussed herein. In some embodiments, the polymer is configured to release the active pharmaceutical ingredient over a time period ranging from about 1 hour to about 168 hours. In some embodiments, the polymer is configured to release the active pharmaceutical ingredient over a time period ranging from 1 hour to 72 hours. In some embodiments, the polymer is configured to release the active pharmaceutical ingredient over a time period ranging from 1 hour to 24 hours.

In some embodiments, the polymer is configured to release the active pharmaceutical ingredient over time in an area surrounding or adjacent to prosthesis 14 (such as, for example, within 3 inches in all dimensions). In some embodiments, the polymer is configured such that there is no release of the active pharmaceutical ingredient for the first week after implantation, and then the polymer releases the active pharmaceutical ingredient for 1 hour to 90 or more days. In some embodiments, the polymer is configured to release the active pharmaceutical ingredient for up to 30 days. In some embodiments, the polymer is configured to release the active pharmaceutical ingredient for up to 90 days. In some embodiments, the polymer is configured to release the active pharmaceutical ingredient for longer than 90 days. In some embodiments, the polymer is configured to release between about 40% to about 100% of the active pharmaceutical ingredient over a period of at least about 30 hours. In some embodiments, the polymer is configured to release 60% to about 100% of the active pharmaceutical ingredient over a period of at least about 30 hours. In some embodiments, the polymer is configured to release between about 65% to about 100% of the active pharmaceutical ingredient over a period of at least about 36 hours. In some embodiments, the polymer is configured to release 80% to about 100% of the active pharmaceutical ingredient over a period of at least about 36 hours. In some embodiments, the polymer is configured to release between about 60% to about 100% of the active pharmaceutical ingredient over a period of at least about 48 hours. In some embodiments, the polymer is configured to release 80% to about 100% of the active pharmaceutical ingredient over a period of at least about 48 hours. In some embodiments, the polymer is configured to release between about 60% to about 100% of the active pharmaceutical ingredient over a period of at least about 60 hours. In some embodiments, the polymer is configured to release 80% to about 100% of the active pharmaceutical ingredient over a period of at least about 60 hours. In some embodiments, the polymer is configured to release 80% to about 100% of the active pharmaceutical ingredient within 48 hours. In some embodiments, the polymer is configured to release 80% to about 100% of the active pharmaceutical ingredient within 24 hours.

In some embodiments, the polymer is configured to release no more than 60% of the active pharmaceutical ingredient within 24 hours. In some embodiments, the polymer is configured to release no more than 90% of the active pharmaceutical ingredient after 60 hours. In some embodiments, the polymer is configured to release no more than 50% of the active pharmaceutical ingredient within 12 hours. In some embodiments, the polymer is configured to release between about 40% to about 90% of the active pharmaceutical ingredient between 12 and 24 hours. In some embodiments, the polymer is configured to release between about 60% to about 100% of the active pharmaceutical ingredient between 24 and 36 hours. In some embodiments, the polymer is configured to release between about 65% to about 100% of the active pharmaceutical ingredient between 36 and 48 hours. In some embodiments, the polymer is configured to release between about 70% to about 100% of the active pharmaceutical ingredient between 48 and 60 hours.

Figure 4:
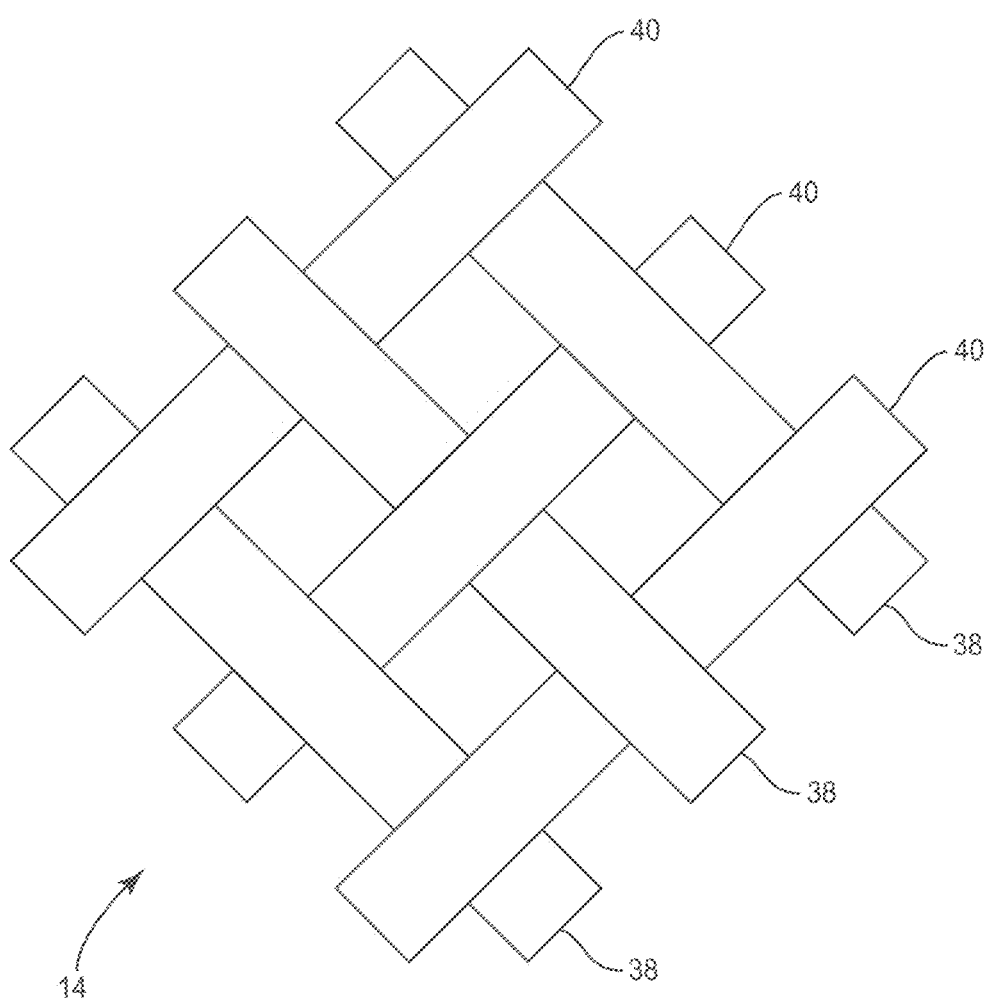
FIG. 4 is a magnified view of a portion of a component of the system shown in FIG. 1.

In some embodiments, pouch 22 and/or tube 28 are made from a polymer, such as, for example, one or more of the polymers discussed herein, wherein the polymer comprises a plurality of strips that are braided to form prosthesis, as shown in FIG. 4. In some embodiments, tube 28 is braided and pouch 22 is not braided. In some embodiments, the strips are braided and/or woven to form a regular pattern. In some embodiments, the strips are braided and/or woven to form a diamond pattern. In some embodiments, the strips are braided and/or woven to form a Hercules pattern. In some embodiments, the strips are braided and/or woven to form a triaxial braid. In some embodiments, the strips are braided and/or woven to form a biaxial braid, such as for example, the common biaxial braid shown in FIG. 4. In some embodiments, the biaxial braid is a diamond biaxial braid. In some embodiments, the biaxial braid is a Hercules biaxial braid.

The common biaxial braid shown in FIG. 4 may be formed as a cylindrical, helically wound braid to form tube 28 and/or pouch 22. As such, pulling tube 28 and/or pouch 22 will lengthen and narrow tube 28 and/or pouch 22 similar to a Chinese finger trap. The length of tube 28 and/or pouch 22 is increased by reducing the angle between strips 38 and strips 40 shown in FIG. 4 at their crossing points. Reducing the angle between strips 38 and strips 40 shown in FIG. 4 at their crossing points reduces the radial distance between opposing ends of tube 28 and/or pouch 22 and the overall circumference of tube 28 and/or pouch 22. The length of tube 28 and/or pouch 22 is decreased by increasing the angle between strips 38 and strips 40 shown in FIG. 4 at their crossing points. Increasing the angle between strips 38 and strips 40 shown in FIG. 4 at their crossing points increases the radial distance between opposing ends of tube 28 and/or pouch 22 and the overall circumference of tube 28 and/or pouch 22.

Forming tube 28 and/or pouch 22 with the common biaxial braid shown in FIG. 4 allows the length of tube 28 and/or pouch 22 to be increased and/or decreased more than if tube 28 and/or pouch 22 were non-braided and/or non-woven, or if tube 28 and/or pouch 22 included braids other than the common biaxial braid shown in FIG. 4. This provides medical practitioners the ability to selectively increase or decrease the amount of the active pharmaceutical ingredient(s) that is released by the polymer along a selected portion of device 12. For example, if it is desired to increase the amount of the active pharmaceutical ingredient(s) that is released by the polymer along all or a portion of tube 28, the length of tube 28 may be decreased by pushing end 30 toward end 32, or vice versa, thus increasing the angle between strips 38 and strips 40 shown in FIG. 4 at their crossing points. Likewise, if it is desired to increase the amount of the active pharmaceutical ingredient(s) that is released by the polymer along all or a portion of pouch 22, the length of pouch 22 may be decreased by pushing opposite ends of pouch 22 toward one another, thus increasing the angle between strips 38 and strips 40 shown in FIG. 4 at their crossing points. Alternatively, if it is desired to decrease the amount of the active pharmaceutical ingredient(s) that is released by the polymer along all or a portion of tube 28, the length of tube 28 may be increased by pulling end 30 away from end 32, or vice versa, thus decreasing the angle between strips 38 and strips 40 shown in FIG. 4 at their crossing points. Likewise, if it is desired to decrease the amount of the active pharmaceutical ingredient(s) that is released by the polymer along all or a portion of pouch 22, the length of pouch 22 may be increased by pulling opposite ends of pouch 22 away from one another, thus decreasing the angle between strips 38 and strips 40 shown in FIG. 4 at their crossing points.

In some embodiments, strips 38 and strips 40 all include the same active pharmaceutical ingredient, such as, for example, one or more of the active pharmaceutical ingredients discussed herein. For example, each of strips 38 and strips 40 may include the same active pharmaceutical ingredient. In some embodiments, strips 38 and strips 40 may include different amounts of the same active pharmaceutical ingredient. For example, strips 38 may include a first amount of the active pharmaceutical ingredient and strips 40 may include more or less of the same active pharmaceutical ingredient. In some embodiments, some of strips 38, strips 40 include a first active pharmaceutical ingredient, such as, for example, one or more of the active pharmaceutical ingredients discussed herein and some of strips 38, strips 40 include a second active pharmaceutical ingredient, such as, for example, one or more of the active pharmaceutical ingredients discussed herein, wherein the second active pharmaceutical ingredient is different than the first pharmaceutical ingredient. For example, each of strips 38 may include the first pharmaceutical ingredient and each of strips 40 may include the second pharmaceutical ingredient.

As discussed herein, end 30 defines a first section of tube 28, and end 32 defines a second section of tube 28 that is coupled to the first section. It is envisioned that end 30 may include one or a plurality of sections and that end 32 may include one or a plurality of sections. Each of the sections may be made of a polymer, such as, for example, one or more of the polymers discussed herein. In some embodiments, the sections each include the same active pharmaceutical ingredient, such as, for example, one or more of the active pharmaceutical ingredients discussed herein. It is envisioned that the amount of the active pharmaceutical ingredient may vary in the different sections. That is, one or more of the sections may include more or less of an active pharmaceutical ingredient than other sections. It is also envisioned that the sections may be configured to release an active pharmaceutical ingredient at different rates. For example, at least one of the sections may be configured to release an active pharmaceutical ingredient over a shorter or longer period of time than at least one of the other sections and/or delay the release of an active pharmaceutical ingredient for a shorter or longer period of time than at least one of the other sections. For example, one of the sections may be configured to release an active pharmaceutical ingredient upon implantation, another one of the sections may be configured to begin to release an active pharmaceutical ingredient after a period of time following implantation, such as, for example, 2 weeks after implantation. It is envisioned that one or more of the sections may be configured to begin to release an active pharmaceutical ingredient after a longer period of time following implantation, such as, for example, 4 weeks after implantation. This configuration allows different sections to release an active pharmaceutical ingredient starting at different times following implantation which allows prosthesis 14 to be customized to treat or prevent different types of infections or infections having different causes. For example, the section or sections that is/are configured to release an active pharmaceutical ingredient upon implantation may release one or more active pharmaceutical ingredient upon implantation over a period of time to treat or prevent initial infecting bacteria and the section or sections that is/are configured to begin releasing an active pharmaceutical ingredient after a certain amount of time following implantation may release one or more active pharmaceutical ingredient after a period of time to treat or prevent infection caused by another source, such as, for example, an infected tooth. In some embodiments, at least one of the sections includes a different active pharmaceutical ingredient than one or more of the other sections. For example, at least one of the sections may include rifampin and minocycline and one or more of the other sections may include an active pharmaceutical ingredient that does not include rifampin and/or minocycline.

In some embodiments, at least a portion of prosthesis 14, such as, for example, tube 28 is made from a metal that is coated with a polymer, such as, for example, one or more of the polymers disclosed herein. In some embodiments, at least a portion of prosthesis 14, such as, for example, tube 28 is made from a shape memory material that is coated with a polymer, such as, for example, one or more of the polymers disclosed herein.

Figure 5:
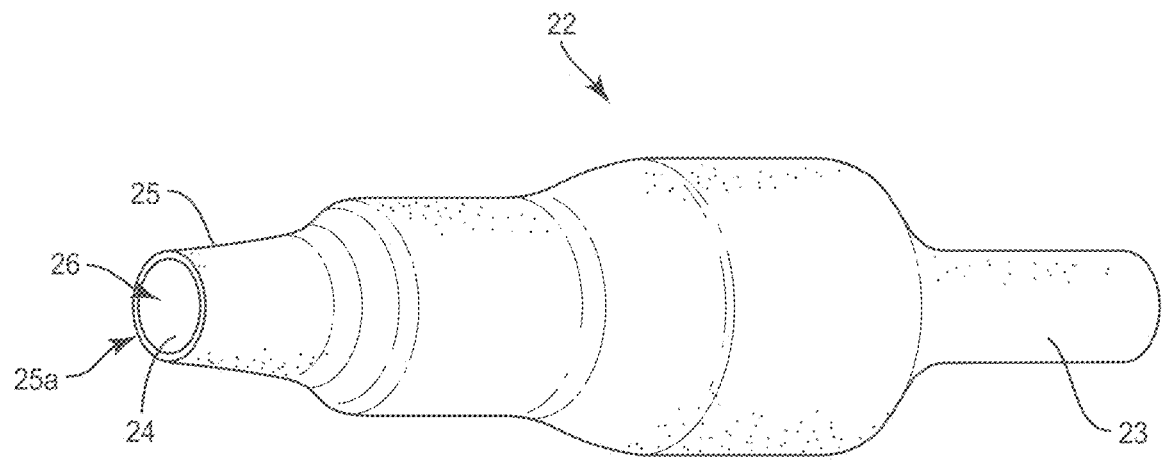
FIG. 5 is a perspective view of a portion of one embodiment of a component shown in FIG. 1 in accordance with the principles of the present disclosure.

In some embodiments, pouch 22 is tapered at ends 23, 25 of pouch 22. That is, ends 23, 25 each have a diameter that is less than a diameter of pouch 22 between ends 23, 25, as shown in FIG. 3. As such, opening 23a in end 23 and opening 25a in end 25 each have a diameter that is less than a diameter of cavity 26 between ends 23, 25. In some embodiments, pouch 22 has a uniform diameter along an entire length of pouch 22. In such embodiments, cavity 26 has a maximum diameter that is equal to a maximum diameter of opening 23a in end 23 and a maximum diameter of opening 25a in end 25. In some embodiments, pouch 22 may have different diameters along the length of pouch 22, as shown in FIGS. 5 and 6, for example. It is envisioned that the size and shape of pouch 22 can be configured such that selected portions of device 12 are positioned within cavity 26. For example, pouch 22 can be configured to fit at least a portion of pump 16, valve 17, valve 19, conduit 13 and/or conduit 15 within cavity 26.

In some embodiments, tube 28 may have a uniform diameter along the entire length of tube 28, as shown in FIG. 3. In some embodiments, tube 28 may have a diameter that increases or decreases along the entire length of tube 28. For example, tube 28 may be tapered from end 30 to end 32 or from end 32 to end 30. In some embodiments, tube 28 is undulating along the length of tube 28.

Prosthesis 14 may include a plug, such as, for example, a ring 42 that is positioned about a portion of tube 28 between end 30 of tube 28 and end 32 of tube 28. Ring 42 is configured to be positioned at an incision site, such as, for example, at incision I to prevent, mitigate and/or treat infection at incision I. In some embodiments, ring 42 is formed separately from tube 28 and is coupled to tube 28 by bonding or adhesive to fix ring 42 to tube 28. In some embodiments, ring 42 is removeably coupled to tube 28 to allow ring 42 to be selectively positioned along the length of tube 28. In some embodiments, ring 42 is integrally formed with tube 28 such that ring 42 cannot be removed from tube 28 without cutting ring 42 from tube 28, for example. Ring 42 includes a diameter that allows ring 42 to cover incision I and engage skin of the patient that incision I extends through. Ring 42 may be formed from a material that is different than the material that forms tube 28. In some embodiments, ring 42 is formed from a polymer, such as, for example, one or more of the polymers discussed herein. In embodiments wherein ring 42 is formed from one or more polymers, the polymer(s) may include an active pharmaceutical ingredient, such as, for example, one or more of the active pharmaceutical ingredients discussed herein.

Figure 7:
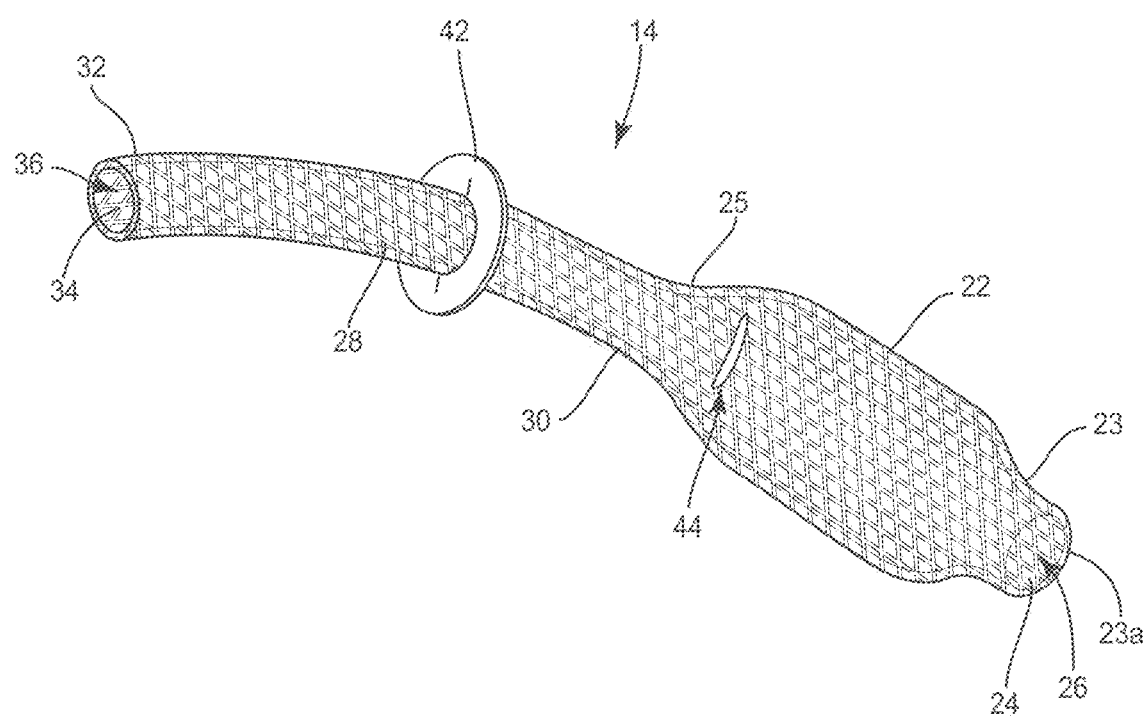
FIG. 7 is a perspective view of components of the system shown in FIG. 1.

In operation and use, at least a portion of device 12 is positioned within cavity 26 of pouch 22. In some embodiments, at least a portion of pump 16, valve 17, valve 19, conduit 13 and/or conduit 15 are positioned within cavity 26. In some embodiments, at least a portion of pump 16, valve 17 and valve 19 are positioned within cavity 26 and conduit 13 and conduit 15 are not positioned within cavity 26. In some embodiments, at least a portion of pump 16 is positioned within cavity 26 and valve 17, valve 19, conduit 13 and conduit 15 are not positioned within cavity 26, as shown in FIG. 1, for example. Valve 17 and conduit 13 extend through opening 23a in end 23 of pouch 22, as shown in FIG. 1. Valve 19 and conduit 15 extend through an opening 44 (FIG. 7) in end 25 of pouch 22. Opening 44 has a diameter that conforms to a diameter of valve 19 such that pouch 22 contacts an outer surface of valve 19 when valve 19 is positioned through opening 44. In some embodiments, opening 44 is created during the formation of pouch 22. That is, opening 44 is pre-formed in pouch 22. In some embodiments, opening 44 is created after pouch 22 is formed by cutting a slit or hole in pouch 22. In some embodiments, opening 44 is reinforced by stitching, for example, that is positioned about opening 44 to prevent opening 44 from expanding when valve 19 and conduit 15 extend through opening 44. In some embodiments, opening 44 is not reinforced to allow opening 44 to expand when valve 19 and conduit 15 extend through opening 44.

Drive line 20 is positioned within passageway 36 of tube 28 such that tube 28 extends over all or a portion of the length of drive line 20, as shown in FIG. 1, for example. In some embodiments, tube 28 extends from pump 16 to battery pack 18 such that tube 28 engages battery pack 18. It is envisioned that tube 28 may cover all or a portion of battery pack 18. In some embodiments, tube 28 extends from pump 16 to a portion of drive line 20 that is positioned between pump 16 and battery pack 18, such that tube 28 is spaced apart from battery pack 18. When drive line 20 is initially positioned within passageway 36 of tube 28, tube 28 has a first length such that tube 28 extends over a selected length of drive line 20. As discussed herein, the selected length may include all or a portion of the entire length of drive line 20. The first length of tube 28 will provide a first amount of one or more active pharmaceutical ingredients along a portion of drive line 20 that is positioned within the patient's body following implantation of device 12 and prosthesis 14 when the polymer(s) that form tube 28 release the active pharmaceutical ingredient(s), such as, for example, one or more of the active pharmaceutical ingredients discussed herein as the polymer(s) degrade(s).

In embodiments wherein prosthesis 14 includes ring 42, ring 42 may be positioned at or adjacent to an incision site, such as, for example, at incision I. In some embodiments, ring 42 is positioned within the patient at the incision site. For example, ring 42 may be positioned under the patient's skin. In such embodiments, tissue ingrowth will help to hold drive line 20 and/or tube 28 in place. In some embodiments, ring 42 is positioned outside of the patient at the incision site. For example, ring 42 may be positioned on the patients skin.

Figure 8:
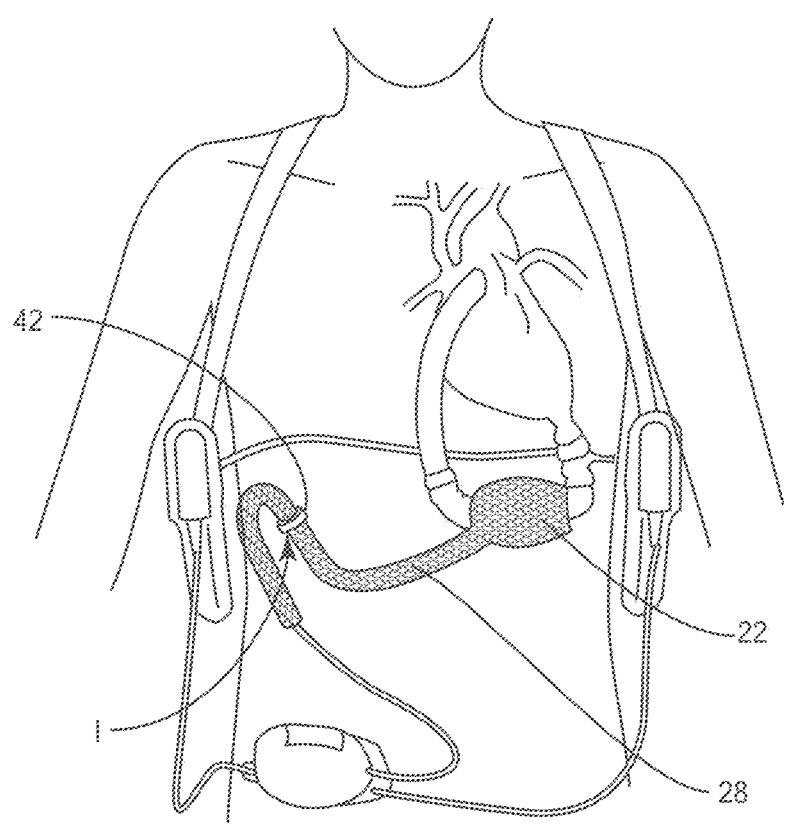
FIG. 8 is a plan view of components of the system shown in FIG. 1.

In some embodiments, device 12 and prosthesis 14 are implanted within the patient while tube 28 has the first length, and the length of tube 28 is not altered following implantation. In some embodiments, tube 28 may then be selectively shortened or lengthened to decrease or increase the length of tube 28 from the first length to a second length. For example, tube 28 may be shortened from the first length shown in FIG. 1 to the second length shown in FIG. 8 by pushing end 32 toward end 30 such that the second length is less than the first length. Alternatively, tube 28 may be lengthened from the first length shown in FIG. 1 to a second length by pulling end 32 away from end 30 such that the second length is greater than the first length. In some embodiments, tube 28 is moved from the first length to the second length before device 12 and prosthesis 14 are implanted within the patient. In some embodiments, tube 28 is moved from the first length to the second length after device 12 and prosthesis 14 are implanted within the patient.

It is envisioned that the second length of tube 28 may be determined based upon the amount of active pharmaceutical ingredient(s) desired to be released along a portion of drive line 20 that is positioned within the patient's body. For example, when it is desired to increase the amount of the active pharmaceutical ingredient(s) to be released along the portion of drive line 20 that is positioned within the patient's body from the first amount, tube 28 may be shortened from the first length shown in FIG. 1 to the second length shown in FIG. 8 by pushing end 32 toward end 30 such that the second length is less than the first length, which will increase the amount and/or concentration of the active pharmaceutical ingredient(s) that will be released along the portion of drive line 20 that is positioned within the patient's body following implantation of device 12 and prosthesis 14. It is envisioned that the amount that tube 28 is shortened may be directly proportional to the amount and/or concentration of the active pharmaceutical ingredient(s) that will be released along the portion of drive line 20 that is positioned within the patient's body following implantation of device 12 and prosthesis 14. That is, the more tube 28 is shortened from the first length, the more the amount and/or concentration of the active pharmaceutical ingredient(s) that will be released along the portion of drive line 20 that is positioned within the patient's body will increase.

When it is desired to decrease the amount of the active pharmaceutical ingredient(s) to be released along the portion of drive line 20 that is positioned within the patient's body from the first amount, tube 28 may be lengthened from the first length shown in FIG. 1 to a second length by pulling end 32 away from end 30 such that the second length is greater than the first length, which will decrease the amount and/or concentration of the active pharmaceutical ingredient(s) that will be released along the portion of drive line 20 that is positioned within the patient's body following implantation of device 12 and prosthesis 14. It is envisioned that the amount that tube 28 is lengthened may be directly proportional to the amount and/or concentration of the active pharmaceutical ingredient(s) that will be released along the portion of drive line 20 that is positioned within the patient's body following implantation of device 12 and prosthesis 14. That is, the more tube 28 is lengthened from the first length, the more the amount and/or concentration of the active pharmaceutical ingredient(s) that will be released along the portion of drive line 20 that is positioned within the patient's body will decrease.

Figure 9:
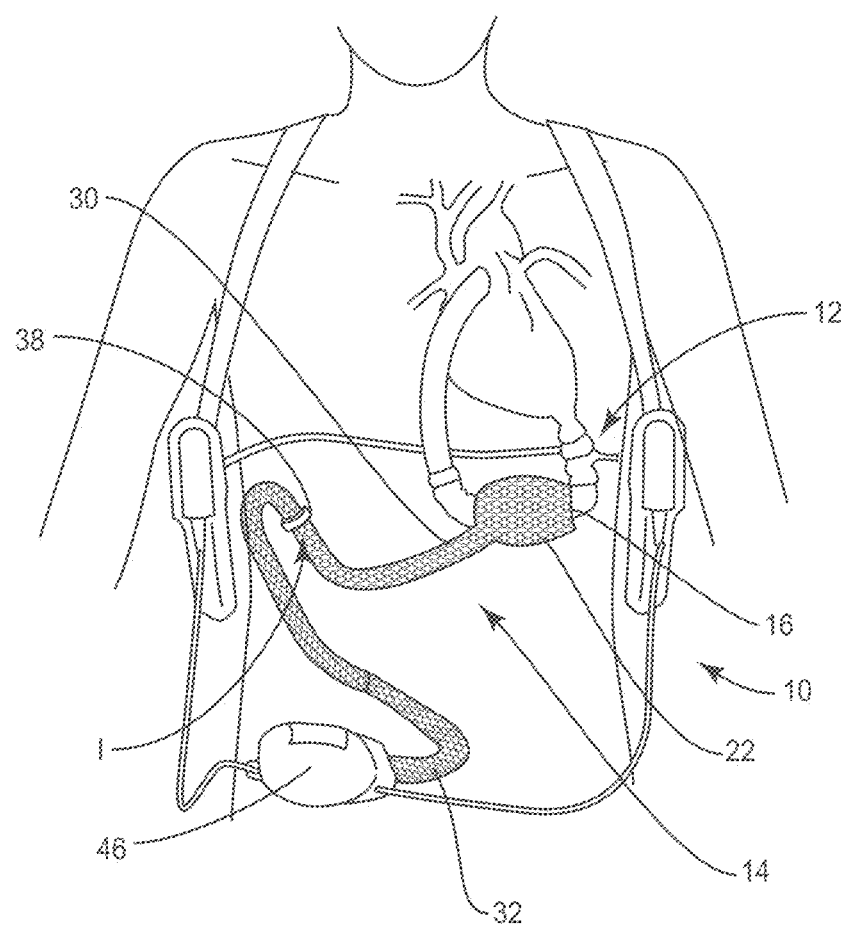
FIG. 9 is a plan view of components of the system shown in FIG. 1.

In some embodiments, tube 28 extends from pump 16 of device 12 to a control unit 46 of device 12, as shown in FIG. 9. As shown in FIG. 9, control unit 46 is located outside of the patient. In some embodiments, tube 28 covers all or a portion of control unit 46. In some embodiments, tube 28 is connected to control unit 46 but does not cover control unit 46. In some embodiments, tube 28 is connected to control unit 46 such that tube 28 cannot be removed from control unit 46 without cutting tube 28 from control unit 46, for example. As such, tube 28 may be bunched up in certain areas along the length of tube 28 where more active pharmaceutical ingredient(s) is/are desired. That is, since end 30 of tube 28 is fixed relative to pump 16 and end 32 of tube 28 is fixed relative to control unit 46, sections along the length of tube 28 may be bunched up or unbunched by moving end 30 toward end 32 or moving end 30 away from end 32, respectively. This allows the amount of the active pharmaceutical ingredient(s) that is released by prosthesis 14 to be selectively adjusted along the length of tube 28.

Figure 10:
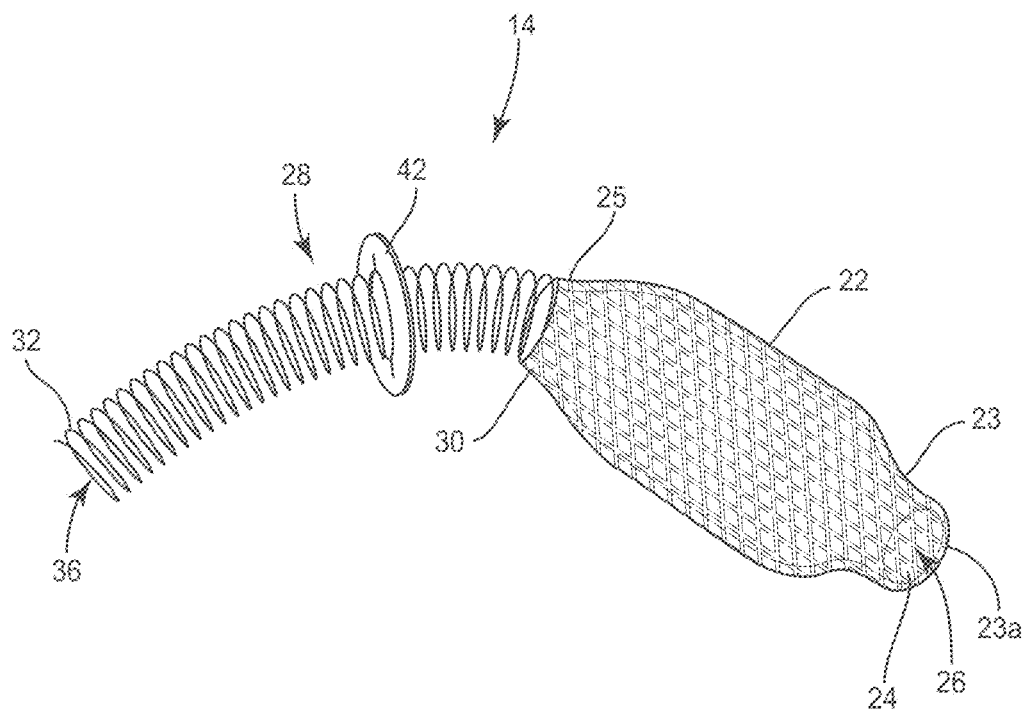
FIG. 10 is a perspective view of one embodiment of components of the system shown in FIG. 1.
Figure 11:
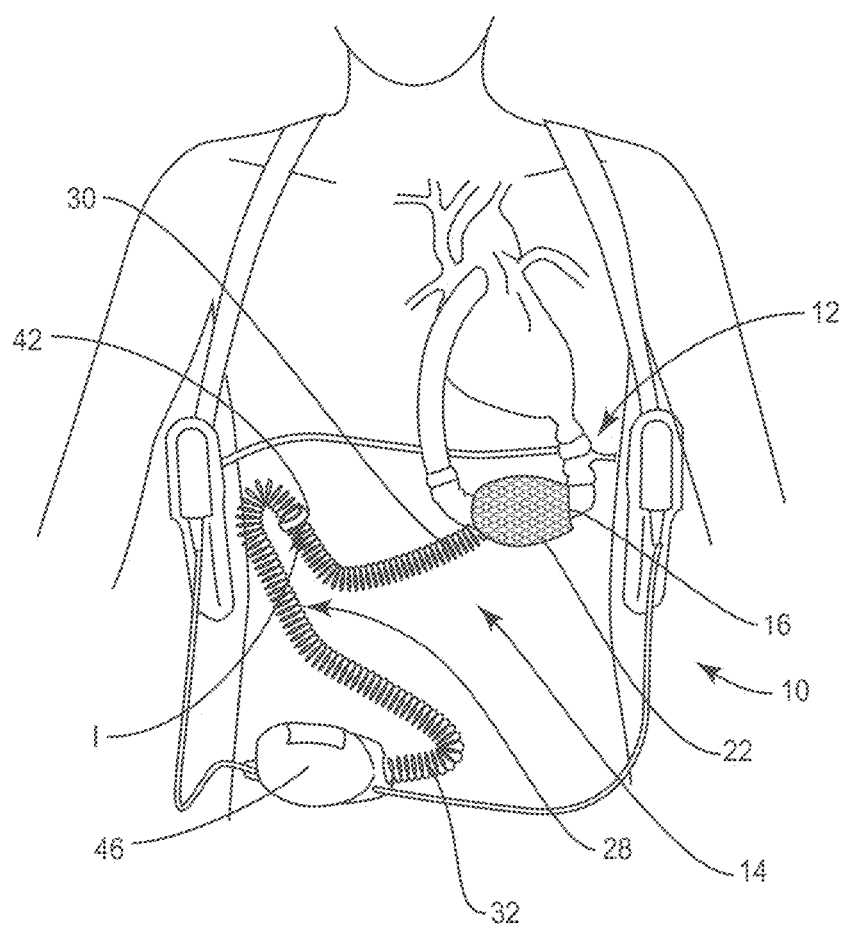
FIG. 11 is a plan view of components of the system shown in FIG. 10.

In some embodiments, pouch 22 is configured as discussed herein and tube 28 is not braided. Rather, tube 28 is a coil, such as, for example, the helically wound coil shown in FIG. 10. As in the embodiments wherein tube 28 is braided, coiled tube 28 may be formed from a polymer, such as, for example, one or more of the polymers discussed herein. The coiled tube 28 is configured to allow for the length of tube 28 to be bunched up or unbunched along selected portions of tube 28 by moving end 30 toward end 32 or moving end 30 away from end 32, respectively. Additionally, it is envisioned that coiled tube 28 may allow the length of tube 28 to expand if battery 18 is dropped, for example. It is envisioned that this will prevent portions of device 12 from moving toward or through incision I if battery 18 is dropped. As shown in FIG. 11, coiled tube 28 shown in FIG. 10 can be configured to extend from pump 16 of device 12 to control unit 46 of device 12. In some embodiments, a portion of end 30 of coiled tube 28 is fixed to pump 16 and a portion of end 32 of the coiled tube 28 is fixed to control unit 46. As such, coiled tube 28 may be bunched up in certain areas along the length of tube 28 where more active pharmaceutical ingredient(s) is/are desired. That is, sections along the length of coiled tube 28 may be bunched up or unbunched by moving end 30 toward end 32 or moving end 30 away from end 32, respectively. This allows the amount of the active pharmaceutical ingredient(s) that is released by prosthesis 14 to be selectively adjusted along the length of coiled tube 28. If battery 18 is dropped or otherwise moved from the position on the patient's body shown in FIG. 11 to another location, such as, for example, the floor of the area the patient is in, the length of coiled tube 28 will increase. This will prevent device 12 from being removed from areas of the patient, such as, for example, his or her heart and/or will prevent portions of device 12 from being disconnected from other portions of device 12. For example, allowing the length of coiled tube 28 to increase if battery 18 is dropped may prevent a first portion of drive line 20 from disconnecting from a second portion of drive line 20 that is connected to the first portion of drive line 20 by a connector, for example. In some embodiments, a ring, such as, for example ring 42 discussed herein, may be positioned about coiled tube 28 in the same manner as with braided tube 28. In some embodiments, coiled tube 28 does not include the ring.

In some embodiments, kits are provided that include one or a plurality of implantable devices, such as, for example, device 12 and one or a plurality of prostheses, such as, for example, prosthesis 14. It is contemplated that each of the prostheses included can have a different configuration. In some embodiments, the prostheses can include different active pharmaceutical ingredients, such as, for example, one or more of the active pharmaceutical ingredients discussed herein. In some embodiments, the prostheses can include different amounts of one or more active pharmaceutical ingredients, such as, for example, one or more of the active pharmaceutical ingredients discussed herein. In some embodiments, the prostheses can include different sizes. For example, the prostheses can have different length tubes, such as, for example, tube 28. The prostheses can have pouches, such as, for example, pouch 22 that are configured to cover different portions of device 12. In some embodiments, the prostheses can include different shapes. In some embodiments, the kit includes instructions for use.

EXAMPLES 2 cm×2 cm pieces were cut from glycoprene mesh which was pre-coated with a polymer layer containing the two antibiotics rifampin and minocycline. The average device weight was 30 mg.

4 pieces of the mesh were placed in separate vials and 20 mL of PBS buffer (pH 7.4) were added. The vials were placed in a heated oven at 37° C. After 1, 2, 4, 7 and 24 hours, the buffer was sampled and analyzed by HPLC for Rifampin and Minocycline. At the 2 hr. and 7 hr. points, the buffer was removed and replaced with fresh 20 mL of buffer and the drug content analyzed after 24 hrs.

An additional 4 samples were placed in 5 mL buffer and analyzed as described above.

Figure 12:
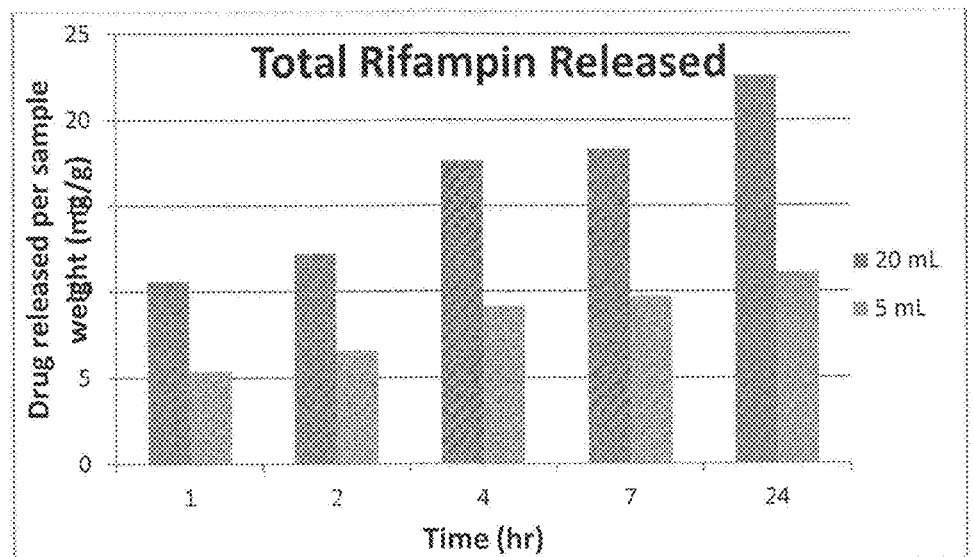
FIG. 12 Graph showing amount of Rifampin eluted over time.
Figure 12A:
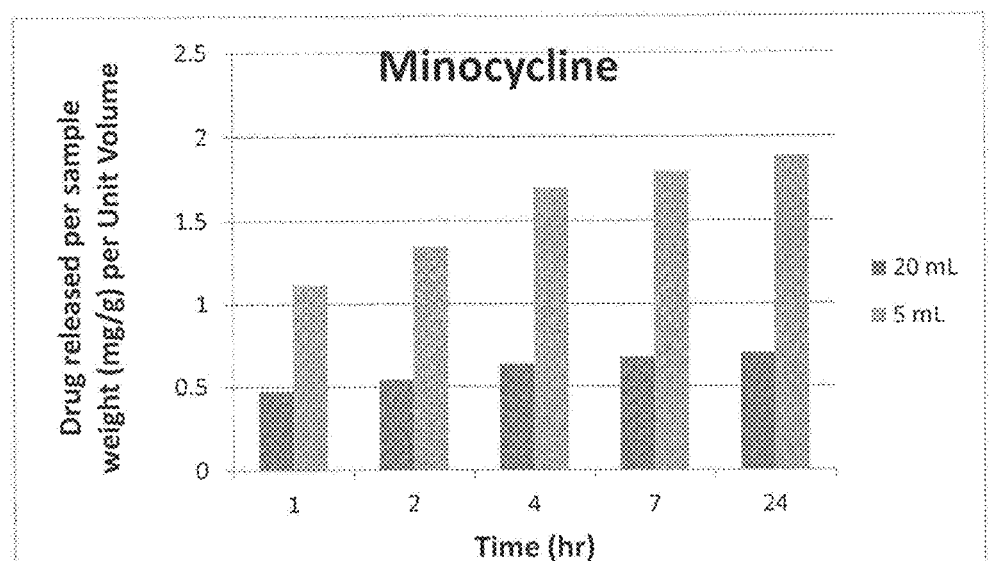
FIG. 12A Graph showing amount of Minocycline eluted over time.

The total amount of drug eluted (normalized to device weight in grams) at various time points are plotted in Graph 1 (FIG. 12) and Graph 2 (FIG. 12A).

Higher amounts of Minocycline and Rifampin are eluted into the buffer when the buffer volume is 20 mL compared to 5 mL.

Figure 12B:
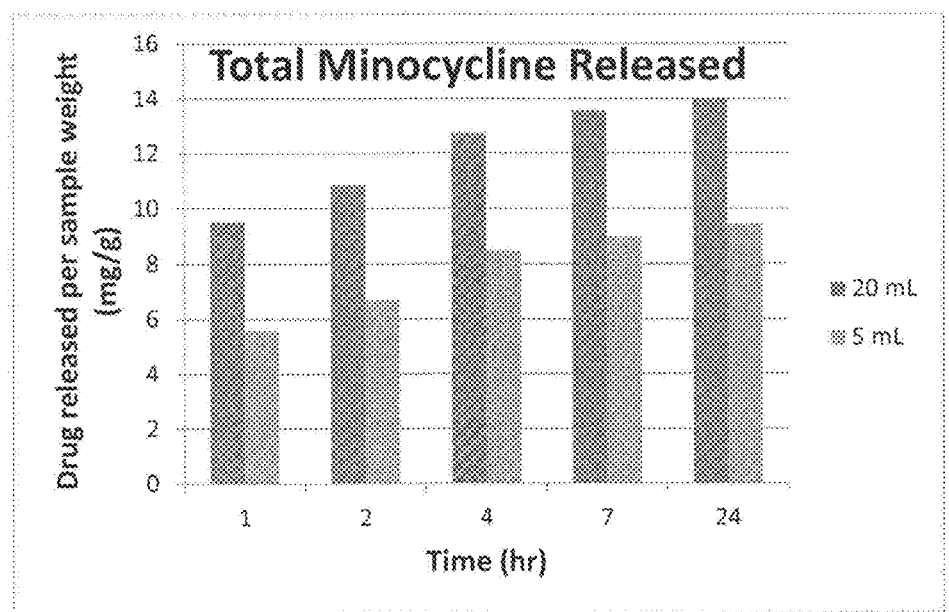
FIG. 12B Graph showing amount of Rifampin per unit volume of buffer overtime.
Figure 12C:
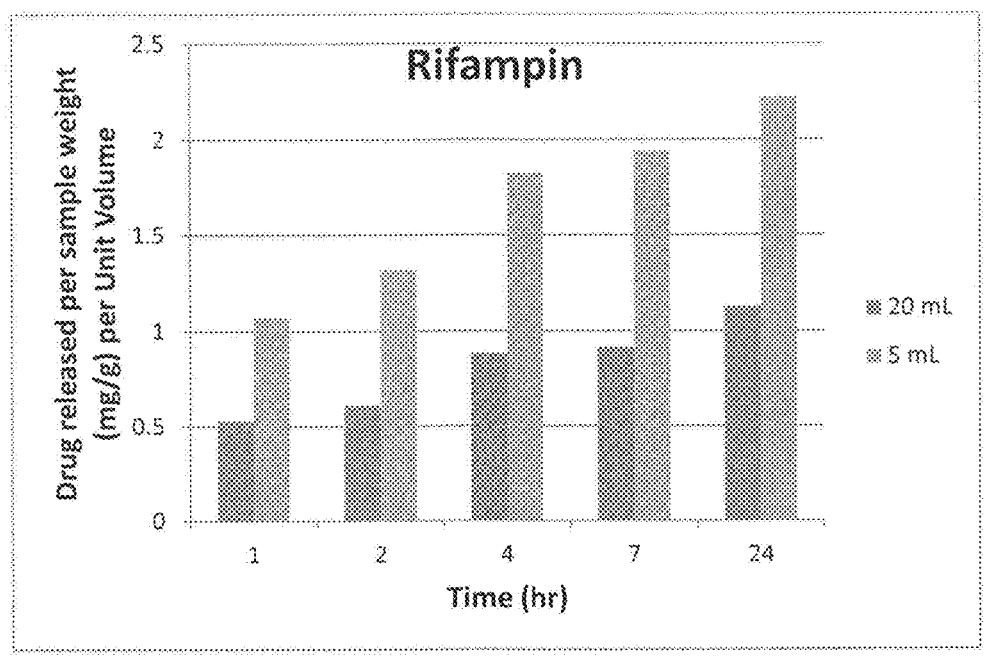
FIG. 12C Graph showing amount of Minocycline per unit volume of buffer over time.

In Graph 3 (FIG. 12B) and Graph 4 (FIG. 12C), the data is replotted to show the amount of drug per unit volume of buffer at various time points.

When the device is in the extended state, more of the surface will be in contact with the tissue providing a larger area and hence larger volume of interstitial for drugs to be eluted into. Hence the tissue concentration will be lower. When the device is in the contracted state, less of the surface will be in contact with the tissue providing a smaller area and hence smaller volume of interstitial fluids for drugs to be eluted into. Hence the tissue concentration will be higher, even though the total amount of drug eluted maybe smaller. This is represented in the in vitro data from Graphs 3 and 4.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A medical prosthesis comprising:
   a tube having a length between a first end and a second end, the tube comprising a plurality of first strips and a plurality of second strips that are braided with the first strips to provide the tube with a mesh configuration defined by gaps between adjacent first strips and between adjacent second strips, the first strips comprising a first polymer, the second strips comprising a second polymer, the first polymer comprising a first drug, the second polymer comprising a second drug, the second drug being different than the first drug,
   wherein the tube is configured to be manipulated to selectively increase and decrease the length of the tube.

2. A medical prosthesis as recited in claim 1, wherein the strips are woven in a biaxial braid.

3. A medical prosthesis as recited in claim 1, wherein the first drug comprises rifampin and minocycline and the second drug comprises a hemostat.

4. A medical prosthesis as recited in claim 1, wherein the first drug is selected from the group consisting of antibiotics and anesthetics and the second drug is selected from the group consisting of anti-cancer drugs and hemostats.

5. A medical prosthesis as recited in claim 1, wherein the first drug is rifampin and the second drug is minocycline.

6. A medical prosthesis as recited in claim 1, wherein the tube comprises a first section along the length of the tube and a second section along the length of the tube, the second section being coupled to the first section, the first section comprising the first drug and the second drug and the second section comprising a third drug that is different than the first drug and the second drug.

7. A medical prosthesis as recited in claim 1, wherein at least one of the polymers comprises a tyrosine-derived polyarylate.

8. A medical prosthesis as recited in claim 7, wherein the tyrosine-derived polyarylate is from the P22-xx family.

9. A medical prosthesis as recited in claim 8, wherein the tyrosine-derived polyarylate from the P22-xx family is P22-27.5.

10. A system comprising:
the medical prosthesis recited in claim 1; and
an implantable medical device,
wherein the medical prosthesis comprises a pouch coupled to the first end of the tube, the pouch comprising an inner cavity that is in communication with a passageway defined by the tube, the pouch comprising the polymer and the at least one drug, and
wherein the implantable medical device is a left ventricular assist device comprising a pump and a drive line that is connected to the pump, the pouch covering at least a portion of the pump and the tube covering at least a portion of the drive line.

11. A method of preventing, mitigating, or treating infection, the method comprising:
positioning a pump of an implantable medical device within the medical prosthesis recited in claim 1;
positioning a drive line of the implantable medical device within the tube, the drive line comprising an electrical wire that is connected to the pump; and
implanting the implantable medical device within a patient such that a portion of the drive line and a battery of the implantable medical device are positioned outside of the patient.

12. A method as recited in claim 11, wherein:
the method further comprises moving the first end relative to the second end to increase or decrease the length of the tube.

13. A method as recited in claim 11, wherein:
the medical prosthesis comprises a ring positioned about the tube; and
implanting the implantable medical device comprises attaching the ring at a point in which the drive line enters the patient.

14. A medical prosthesis as recited in claim 1, wherein the first end defines a first opening and second end defines a second opening, the first opening being configured for disposal of a first component of a medical device, the second opening being configured for disposal of a second component of the medical device.

15. A medical prosthesis as recited in claim 1, wherein an inner surface of the tube defines a passageway, the gaps defining openings that are in communication with the passageway.

16. A medical prosthesis comprising:
a tube having a maximum length defined by a distance from a first end surface of the tube to an opposite second end surface of the tube, the tube comprising a plurality of first strips and a plurality of second strips, the second strips being braided with the second strips from the first end surface to the second end surface, the first strips comprising a first polymer, the second strips comprising a second polymer, the first polymer comprising a first drug, the second polymer comprising a second drug, the second drug being different than the first drug,
wherein the tube is configured to be manipulated to increase the length by reducing angles between the first strips and the second strips at crossing points of the first and second strips and decrease the length by increasing angles between the first strips and the second strip at the crossing points of the first and second strips.

17. A medical prosthesis as recited in claim 16, wherein the first drug comprises rifampin and the second drug comprises minocycline.

18. A medical prosthesis as recited in claim 16, wherein the first drug comprises a first amount of rifampin and minocycline and the second drug comprises a second amount of rifampin and minocycline, the second amount being different than the first amount.

19. A medical prosthesis as recited in claim 16, wherein the end surfaces are each configured to be removably coupled to a medical device.

20. A medical prosthesis as recited in claim 16, wherein the first strips and the second strips provide the tube with a mesh configuration defined by gaps between adjacent first strips and between adjacent second strips.

* * * * *